United States Patent [19]

Rizkalla

[11] Patent Number: 4,551,560

[45] Date of Patent: Nov. 5, 1985

[54] THERMALLY-INDUCED HYDROLYSIS OF ACETAL

[75] Inventor: Nabil M. Rizkalla, River Vale, N.J.

[73] Assignee: The Halcon SD Group, Inc., New York, N.Y.

[21] Appl. No.: 669,708

[22] Filed: Nov. 9, 1984

[51] Int. Cl.[4] .................. C07C 45/51; C07C 47/02
[52] U.S. Cl. .................... 568/465; 568/484; 568/485; 568/907
[58] Field of Search .............. 568/458, 465, 484, 485, 568/486, 902, 903, 906, 907

[56] References Cited

U.S. PATENT DOCUMENTS

| | | | |
|---|---|---|---|
| 3,676,500 | 7/1972 | Mantell et al. | 568/486 |
| 3,897,503 | 7/1975 | Wessendorf et al. | 568/486 |
| 4,071,563 | 1/1978 | Kummer et al. | 568/486 |

*Primary Examiner*—Werren B. Lone
*Attorney, Agent, or Firm*—William C. Long; Riggs T. Stewart; Daniel R. Zirker

[57] ABSTRACT

A process for the selective, thermally-induced hydrolysis of acetals to the corresponding aldehydes and alcohols is disclosed, involving heating and pressurizing a substantially acid-free acetal containing solution to effect the rapid hydrolysis of the acetals without significant harm to the remaining reaction system components, and removing the treated solution from the reaction zone as product.

11 Claims, No Drawings

THERMALLY-INDUCED HYDROLYSIS OF ACETAL

BACKGROUND OF THE INVENTION

1. Field of the Invention

This invention relates to a process for the hydrolysis of acetals to the corresponding aldehydes and alcohols and, more particularly, to a direct, simple method for the selective hydrolysis of acetal to acetaldehyde and methanol in the presence of a variety of other reaction effluent components, typically those resulting from the reductive carbonylation of an alcohol feedstock, e.g., methanol.

2. Description of the Prior Art

Homologation reactions typically involve the reaction of a selected alcohol with carbon monoxide and hydrogen under elevated temperatures and superatmospheric pressures, in the presence of a suitable catalyst, e.g., a metal carbonyl complex. In the reductive carbonylation of methanol, the resulting reaction effluent contains a substantial amount of acetal byproduct, e.g., dimethoxy ethane, acetaldehyde diethylacetal and the like, as well as unreacted methanol, acetaldehyde and ethanol, together with water, methyl acetate, catalyst and a solvent. Similar effluents have been treated in the prior art by heating the solution in aqueous acid, or in the presence of another suitable catalyst, to catalyze the hydrolysis of the resulting acetal in order to obtain the desired products, acetaldehyde and alcohol. Typical of such systems is U.S. Pat. No. 4,388,154, which discloses a process wherein acetaldehyde and methanol are obtained from reaction effluents of the homologation of methanol and which, in addition to acetaldehyde, contain acetaldehyde dimethylacetal, methanol, methyl acetate, water and catalyst. The problem with such a process is that the chosen hydrolysis catalyst, e.g., an acid, fosters competing unwanted side reactions with the acetal and/or aldehyde. Also, almost all catalysts are acidic in nature, and usually facilitate corrosion by their presence in the reaction zone. Finally, the prior art systems have a tendency to hydrolyze any esters present in the system, e.g., the presence of the catalyst enhances the saponification of the esters and can lead to the formation of products such as acetic acid, which greatly complicates the ensuing recovery of the desired components present in the system.

Accordingly, it is an object of the present invention to provide a process for the effective, yet simple and selective hydrolysis of acetals while in the presence of a wide variety of other reaction components.

It is another object of the invention to provide a process for the hydrolysis of dimethoxy ethane to acetaldehyde and methanol in an effluent stream resulting from the reductive carbonylation of methanol.

It is still another object of this invention to provide a process for the hydrolysis of acetal which is formed during the reductive carbonylation of methanol, which process substantially eliminates unwanted side reactions, is substantially corrosion-free, and proceeds at desired reaction rates.

SUMMARY OF THE INVENTION

In accordance with the aforementioned objects, the invention comprises a simple, economic method for the substantially selective thermally-induced hydrolysis of acetals to the corresponding lower, i.e., about $C_2$ to $C_6$ aldehydes and alcohols, comprising forming a substantially catalystfree, acetal-containing solution, preferably, if necessary, by separating, e.g., distilling the acetal-containing solution from any acidic catalyst component present, e.g., an effluent stream from the reductive carbonylation of methanol; heating and pressurizing the acetal-containing solution to a sufficient temperature, e.g., at least about 140° C., preferably from about 150° to 250° C. and a corresponding pressure of about 50–5000 psia, preferably 100–2000 psia to effect the substantial hydrolysis of the acetal present in the solution to the corresponding aldehyde and alcohol; the reaction occurring in the presence of a suitable e.g., from 200/1 to 0/1/1 and preferably about 10/1 moles $H_2O$/mole acetal, amount of water; removing the resultant, e.g., substantially reduced in acetal concentration, liquid solution as product. The process further features the substantial elimination of competing undesired side reactions catalyzed by the usually present catalyst, enjoys substantially corrosion-free operation, and particularly fast reaction rates.

DETAILED DESCRIPTION OF THE INVENTION

The process of the present invention can, in the broadest embodiment, be utilized to effect the thermally-induced hydrolysis of acetals to form the corresponding lower, i.e., $C_2$ to about $C_4$ to $C_6$ aldehydes and alcohols from a variety of catalyst and noncatalyst containing reaction effluents, and is particularly suited for treating reductive carbonylation effluent streams, particularly those resulting from the reductive carbonylation of methanol. Such effluents, in the prior art, have been subjected to heating when combined with an aqueous acid containing solution, or a catalyst containing composition, in order to effectively catalyze the hydrolysis of the acetal to aldehyde and alcohol. These systems, however, are flawed, either by the presence of harmful side reactions catalyzed by the hydrolysis catalyst, or by catalyst-induced corrosion, or by the presence of undesired catalytic-induced hydrolysis of the esters present.

The process of the invention is predicated around the surprising discovery that by heating for a sufficient time the reductive carbonylation effluent stream to at least a certain temperature and a corresponding pressure sufficient to maintain the solution substantially in the liquid phase in the absence of an acidic catalyst component, the catalyst preferably having been separated, if it was initially present, from the liquid effluent most preferably along with the particular carbonylation solvent present, the acetals present can be effectively broken down into their corresponding organic components. In a particularly preferred embodiment of the process, a reductive carbonylation effluent of methanol stream, typically containing unreacted methanol, acetaldehyde, ethanol, as well as byproducts acetal, water, methyl acetate, a catalyst such as a carbonyl complex of metals found in Group VIII of the Periodic Table, and a heavy solvent, is first subjected to a flash distillation which separates the reactant and product components in the distillation overhead stream, while the catalyst component, together with the carbonylation solvent, form the distillation bottoms. The distillation overhead is then simply heated to a suitable effective temperature, i.e., at least in excess of 140° C, preferably, from about 150° to 250° C., although both higher and lower temperatures may be permissible, in the broadest embodiment; under a corresponding suitable pressure, e.g., from about 50 to 5000 psia, and preferably from about 100 to 2000 psia, for a time sufficient, e.g., for 0.1 to 300 minutes, preferably about 10 to 200 minutes, to effect the thermal-induced hydrolysis of the acetal present. It is preferred that a satisfactory amount, e.g., from about 0.1 to 200 moles water/mole acetal be present, most preferably about 10 to 1 moles water/mole of acetal; with the addition of a suitable make up water stream available for the enhancement of the hydrolysis reaction rate.

The resulting hydrolysis reaction may be carried out in the presence of any suitable inert gas, e.g., nitrogen. In the absence of catalyst components in the system, it is possible to use a gas that is indigenous to the homologation reaction, e.g., carbon monoxide, hydrogen, methane, their mixtures, and the like. These gases are inert in the hydrolysis reaction. The hydrolysis reaction may also be carried out in either a batch reactor, a boiling pot reactor containing only water or water and solvent, or any other suitable reactor including a continuous system which is adapted to conform with the teachings of this invention.

The resulting thermal hydrolysis of acetal attains a surprisingly high conversion of acetal to aldehyde and alcohol in a very short period of time. Conversions of 80 to about 100% are typically obtained, without significant damage occurring to the other components present in the reaction system during the process.

As has been mentioned above, the disclosed process is further advantageous in that the elimination of the catalyst from the reaction system involving the hydrolysis of the acetal also eliminates the harmful competing side reactions of acetal or aldehyde that would be otherwise catalyzed by its presence. Another advantage is that the absence of the acidic catalyst component substantially eliminates the danger of significant corrosion taking place during the hydrolysis reaction. Also, the thermally-induced hydrolysis of acetals proceeds at a much greater rate than does the thermally-induced hydrolysis of any esters present in the system. Esters such as methyl acetate can accordingly be recovered, virtually unhydrolyzed, by distillation. In contrast, the presence of a catalyst component enhances the saponification of the esters, forming such compounds as acetic acid, which is heavier than the other components of the hydrolysis mixture, and may thereby create difficulties and additional expense in effecting its removal from the system.

EXAMPLES

In the following examples, all parts given are by weight.

EXAMPLE 1

A catalyst-free mixture containing 120 parts of dimethoxy ethane, 120 parts water and 120 parts acetaldehyde was charged to a pressure vessel along with 400 psig of hydrogen. The mixture was heated to 180° C. for one hour. Gas chromatography analysis of the resultant reaction mixture showed it to contain 19.8 parts of dimethoxy ethane, representing an 83.5% conversion of the acetal charged. The effluent contained 71 parts methanol and 169 parts acetaldehyde.

EXAMPLE 2

A catalyst-free mixture containing 175 parts of dimethoxy ethane and 175 parts water was charged to a pressure vessel along with 400 psig of hydrogen. The mixture was heated for one hour at 180° C. G.C. analysis of the reaction effluent showed it to contain 74 parts acetaldehyde, 23.1 parts dimethoxy ethane and 107 parts methanol. This represents an 87% conversion of the charged acetal.

EXAMPLE 3

Example 2 was repeated under a pressure of 1000 psig of hydrogen. The resulting effluent contained 76 parts acetaldehyde, 110 parts methanol and 19.6 parts dimethoxy ethane. This represents an 88.8 conversion of the charged acetal.

EXAMPLE 4

Example 2 was again repeated under a pressure of 300 psig of nitrogen. The resulting effluent contained 74 parts acetaldehyde, 108 parts methanol and 23 parts dimethoxy methane. This represents an 86.9 conversion of the charged acetal.

EXAMPLE 5

Example 2 was again repeated at a temperature of 160° C. The mixture was heated for two hours. G.C. analysis of the resulting reaction mixture showed it to contain 74.6 parts acetaldehyde, 116 parts methanol and 11.5 parts dimethoxy ethane. This represents a 93.4 conversion of the charged acetal.

EXAMPLE 6

A catalyst-free mixture containing 45 parts of dimethoxy ethane, 135 parts per water, 30 parts acetaldehyde, 45 parts methanol, and 45 parts methyl acetate was charged to a pressure vessel with 400 psig of hydrogen. The mixture was heated for one hour at 180° C. G.C. analysis of the reaction effluent showed it to contain 48.1 parts acetaldehyde, 7.8 parts dimethyoxy ethane, 71.7 parts methanol and 44 parts methyl acetate. This represents an 82.7 conversion of the charged acetal.

I claim:

1. A process for the selective-thermally induced hydrolysis of acetals to the corresponding lower non aromatic aldehydes and alcohols of about 2 to 6 carbon atoms, comprising:
   forming a substantially catalyst-free, acetal-containing solution;
   heating and pressurizing the acetal-containing solution to a temperature above about 140° C. and a corresponding pressure ranging from about 50–5000 psia to effect the substantial hydrolysis of the acetal present in the solution to the corresponding non aromatic aldehyde and alcohol of about 2 to 6 carbon atoms; the reaction occurring in a suitable amount of water;
   removing the resultant liquid solution as product.

2. A process as claimed in claim 1 wherein the acetal containing solution is formed by separating the solution from any acidic catalyst component present.

3. A process as claimed in claim 2 wherein the acidic catalyst component is separated from the acetal-containing solution by distillation.

4. A process as claimed in claim 1 wherein the acetal-containing solution is the effluent from the reductive carbonylation of methanol.

5. A process as claimed in claim 1 wherein the acetal-containing solution is heated to about 150°–250° C.

6. A process as claimed in claim 1 wherein the pressure is about 100–2000 psia.

7. A process as claimed in claim 1 wherein the amount of water present in the hydrolysis reaction system ranges from about 200/1 to 0.1/1 moles H$_2$O per mole of acetal.

8. A process as claimed in claim 7 wherein the amount of water present is about 10 moles H$_2$O per mole of acetal.

9. A process as claimed in claim 1 wherein the process is a batch process.

10. A process as claimed in claim 1 wherein the process is a continuous process.

11. A process as claimed in claim 1 wherein dimethoxy ethane is substantially hydrolyzed to acetaldehyde and methanol.

* * * * *